United States Patent [19]

Kawata et al.

[11] Patent Number: 4,619,888

[45] Date of Patent: Oct. 28, 1986

[54] HEAT DEVELOPABLE LIGHT-SENSITIVE MATERIAL

[75] Inventors: Ken Kawata; Yoshiharu Yabuki; Kouzou Sato; Hiroyuki Hirai, all of Minami-ashigara, Japan

[73] Assignee: Fuji Photo Film Co., Ltd., Kanagawa, Japan

[21] Appl. No.: 769,297

[22] Filed: Aug. 26, 1985

[30] Foreign Application Priority Data

Aug. 24, 1984 [JP] Japan ................................ 59-176397

[51] Int. Cl.$^4$ ................................ G03C 1/02
[52] U.S. Cl. .................... 430/353; 430/617; 430/619; 430/620; 430/955; 430/203; 430/570; 430/351
[58] Field of Search ............... 430/617, 619, 955, 203, 430/151, 179, 350, 351, 570, 353, 620

[56] References Cited

U.S. PATENT DOCUMENTS 4,499,172  2/1985  Hirai et al. ........................ 430/955

FOREIGN PATENT DOCUMENTS 909491  10/1962  United Kingdom ................ 430/151

*Primary Examiner*—Won H. Louie

*Attorney, Agent, or Firm*—Sughrue, Mion, Zinn, Macpeak, and Seas

[57] ABSTRACT

A heat developable light-sensitive material comprising a support and a heat developable light-sensitive layer formed thereon can produce images of high density and less fog in a short period of time and has excellent aging stability. The light-sensitive material contains as a base precursor at least one compound selected from the group consisting of compounds represented by formula [I]:

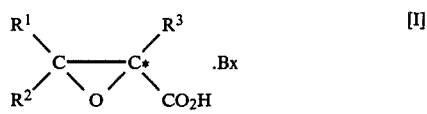

wherein $R^1$ and $R^2$ individually represent hydrogen, alkyl, cycloalkyl, alkenyl, alkynyl, aryl, aralkyl, heterocyclic group, or —$CO_2M$ wherein M represents hydrogen, alkali metal or H.Bx, and $R^1$ and $R^2$ can be joined together to form a ring; $R^3$ represents hydrogen atom, alkyl, cycloalkyl, alkenyl, alkynyl, aralkyl, aryl, or heterocyclic group; x is equal to 1 when B represents a monoacidic base and equal to ½ when B represents a diacidic base; and C* represents an asymmetric carbon atom.

14 Claims, No Drawings

HEAT DEVELOPABLE LIGHT-SENSITIVE MATERIAL

FIELD OF THE INVENTION

This invention relates to a heat developable light-sensitive material containing a base precursor.

BACKGROUND OF THE INVENTION

Heat developable light-sensitive materials often contain bases or base precursors for the purpose of accelerating heat development. Base precursors capable of releasing basic materials upon thermolysis are preferred because of the shelf life of the light-sensitive materials containing the same.

Typical base precursors are described in U.K. Pat. No. 998,949. The preferred base precursors are salts of carboxylic acids with organic bases. The preferred carboxylic acids include trichloroacetic acid, trifluoroacetic acid, etc., and the preferred organic bases include guanidine, piperidine, morpholine, p-toluidine, 2-picoline, etc. A particularly useful base precursor is guanidine trichloroacetate as described in U.S. Pat. No. 3,220,846. Also, preferred are aldonamides as described in Japanese Patent Application Kokai No. 50-22625, which decompose at elevated temperatures to form a base.

However, many prior art base precursors require a relatively long period of time to produce images with accompanying severe fog. As these base precursors are labile in air and humidity, they tend to decompose under normal conditions, undesirably changing the photographic characteristics of the associated light-sensitive materials and substantially reducing the shelf life thereof.

SUMMARY OF THE INVENTION

It is, therefore, an object of this invention to provide a novel and improved heat developable light-sensitive material comprising a base precursor capable of producing images of high density in a short period of time and having an improved shelf life. Another object of this invention is to provide a heat developable light-sensitive material comprising a novel base precursor capable of producing images having high density and less fog.

Still another object of this invention is to provide a heat developable light-sensitive material having excellent aging stability.

We have discovered that the above-described objects of this invention can be attained by a heat developable light-sensitive material containing as a base precursor at least one compound selected from the group consisting of compounds having the formula [I]:

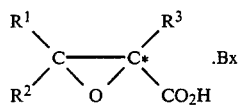

wherein $R^1$ and $R^2$ individually represent a hydrogen atom, a substituted or unsubstituted alkyl group, a substituted or unsubstituted cycloalkyl group, a substituted or unsubstituted alkenyl group, a substituted or unsubstituted alkynyl group, a substituted or unsubstituted aryl group, a substituted or unsubstituted aralkyl group, a substituted or unsubstituted heterocyclic group, or $-CO_2M$ wherein M represents a hydrogen atom, an alkali metal or H.Bx, and $R^1$ and $R^2$ can be joined together to form a ring;

$R^3$ represents a hydrogen atom, a substituted or unsubstituted alkyl group, a substituted or unsubstituted cycloalkyl group, a substituted or unsubstituted alkenyl group, a substituted or unsubstituted alkynyl group, a substituted or unsubstituted aralkyl group, a substituted or unsubstituted aryl group, or a substituted or unsubstituted heterocyclic group;

B represents a monoacidic organic base or diacidic organic base;

x is equal to 1 when B represents a monoacidic base and equal to ½ when B represents a diacidic base; and $C^*$ represents an asymmetric carbon atom to which $R^3$ and $CO_2H$ may be attached in either of the possible configurations.

DETAILED DESCRIPTION OF THE INVENTION

The heat developable light-sensitive material of the present invention comprises as a base precursor a compound having the general formula [I]:

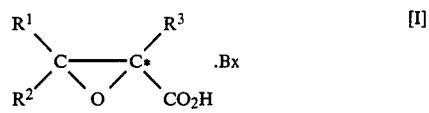

wherein $R^1$, $R^2$, $R^3$, B and x are as defined above. More particularly, $R^1$ and $R^2$ are individually selected from hydrogen atom; substituted or unsubstituted alkyl groups having 1 to 10 carbon atoms; substituted or unsubstituted cycloalkyl groups having 5 to 8 carbon atoms; substituted or unsubstituted alkenyl groups having 2 to 5 carbon atoms; substituted or unsubstituted alkynyl groups having 2 to 5 carbon atoms; substituted or unsubstituted aryl groups such as phenyl, substituted phenyl groups, naphthyl, substituted naphthyl groups, and anthryl group; substituted or unsubstituted 5- and 6-membered hyterocyclic groups such as pyridyl, substituted pyridyl groups, thienyl, substituted thienyl groups, furyl, substituted furyl groups, furfuryl, and substituted furfuryl groups; substituted or unsubstituted aralkyl groups having 7 to 10 carbon atoms; and $-CO_2M$ groups such as carboxyl group, $-CO_2Na$, $-CO_2K$, $-CO_2Cs$, and $-CO_2H.Bx$ where B is an organic base and x is equal to 1 or ½. When $R^1$ and $R^2$ are joined together to form a ring, they may preferably be selected from alkylene groups having 4 to 8 carbon atoms; and alkenylene groups having 4 to 5 carbon atoms wherein another aromatic ring may be condensed to their double bond. Substituents with which $R^1$ and $R^2$ can be substituted may preferably be selected from halogen atoms, alkoxy, nitro, sulfonyl, aryloxy, cyano, acyl, sulfamoyl, carbamoyl, acylamino, ureido, and sulfonylamino groups. It is to be understood that $R^1$ and $R^2$ may be the same or different.

$R^3$ in formula [I] is preferably selected from hydrogen atom; substituted or unsubstituted alkyl groups having 1 to 8 carbon atoms; substituted or unsubstituted cycloalkyl groups having 5 to 8 carbon atoms; substituted or unsubstituted cycloalkyl groups having 5 to 8 carbon atoms; substituted or unsubstituted alkenyl groups having 2 to 5 carbon atoms; substituted or unsubstituted aryl groups such as phenyl and substituted phenyl groups, naphthyl, and substituted naphthyl groups; substituted or unsubstituted aralkyl groups having 7 to 10 carbon atoms; substituted or unsubstituted alkynyl groups having 2 to 5 carbon atoms; and substituted or unsubstituted heterocyclic groups such as pyridyl, substituted pyridyl groups, thienyl, substituted thienyl groups, furyl, substituted furyl groups, furfuryl, and substituted furfuryl groups. The preferred radicals for $R^3$ are hydrogen atom and alkyl groups.

B is selected from organic bases. The preferred organic bases have pKa of at least 9 and a boiling point of at least 100° C., and the most preferred organic bases have pKa of at least 10 and are substantially neither volatile nor smelly at room temperature. Included are guanidines, cyclic guanidines, for example,

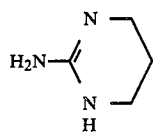

amidines, and cyclic amidines, for example,

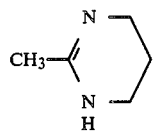

It is further desired that B be hydrophilic and more preferably contain 10 or less carbon atoms in total.

Preferably, B is selected from the group consisting of an aromatic or aliphatic amine, an aromatic or aliphatic diamine, a piperidine, a piperadine, a guanidine, a cyclic guanidine, an amidine, a cyclic amidine, and a tetraalkylammonium hydroxide.

The preferred examples of B are illustrated below.

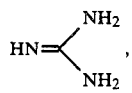 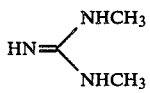

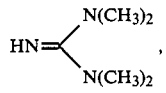

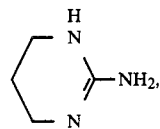

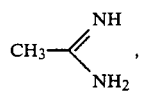

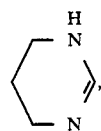 

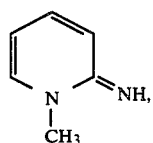

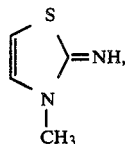

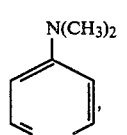

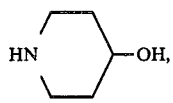

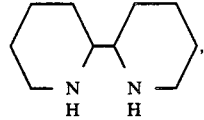

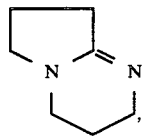

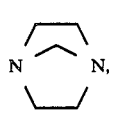

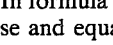

In formula [I], x is equal to 1 when B is a monoacidic base and equal to ½ when B is a diacidic base, and C* represents an asymmetric carbon atom to which no particular optical isomerism is imposed.

Illustrative, but non-limiting examples of the base precursors which can be used in the practice of the present invention are shown below.

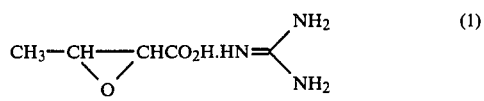 (1)

-continued
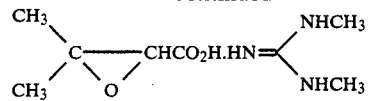 (2)
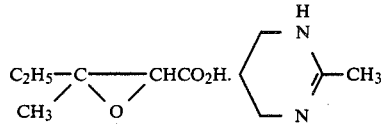 (3)
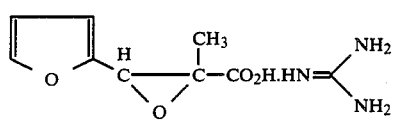 (4)
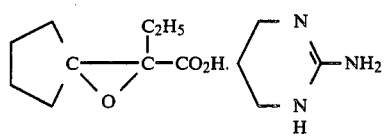 (5)
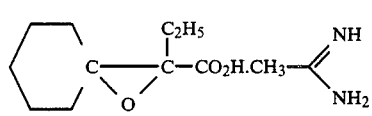 (6)
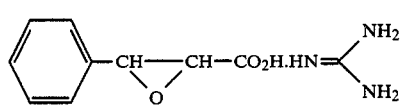 (7)
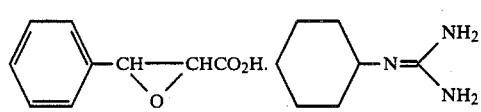 (8)
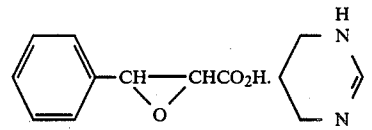 (9)
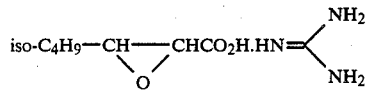 (10)
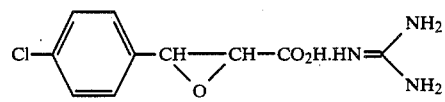 (11)
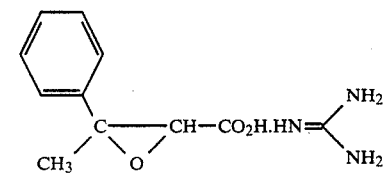 (12)
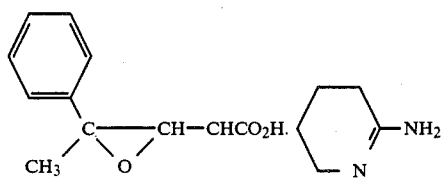 (13)
-continued
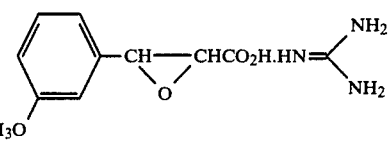 (14)
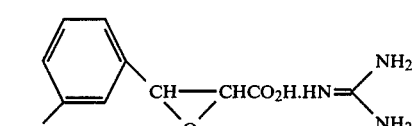 (15)
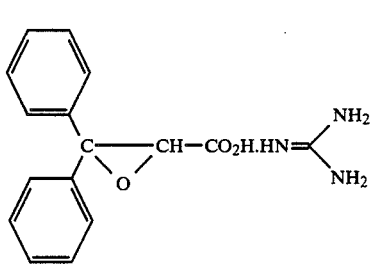 (16)
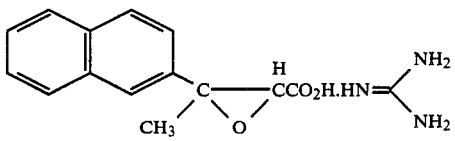 (17)
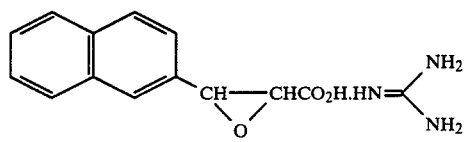 (18)
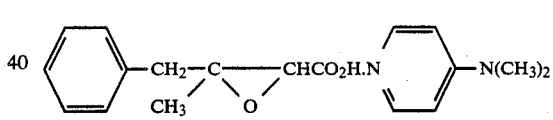 (19)
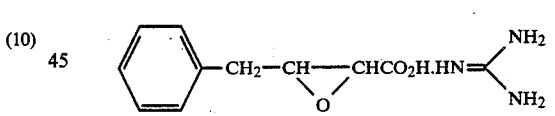 (20)
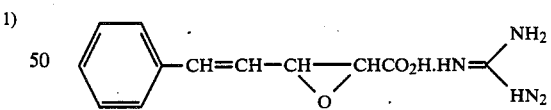 (21)
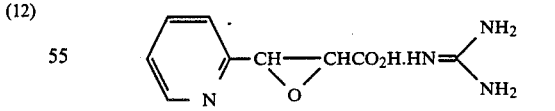 (22)
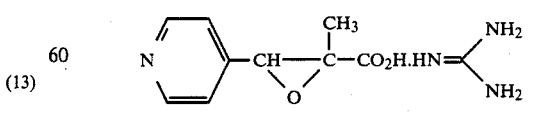 (23)
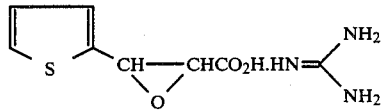 (24)

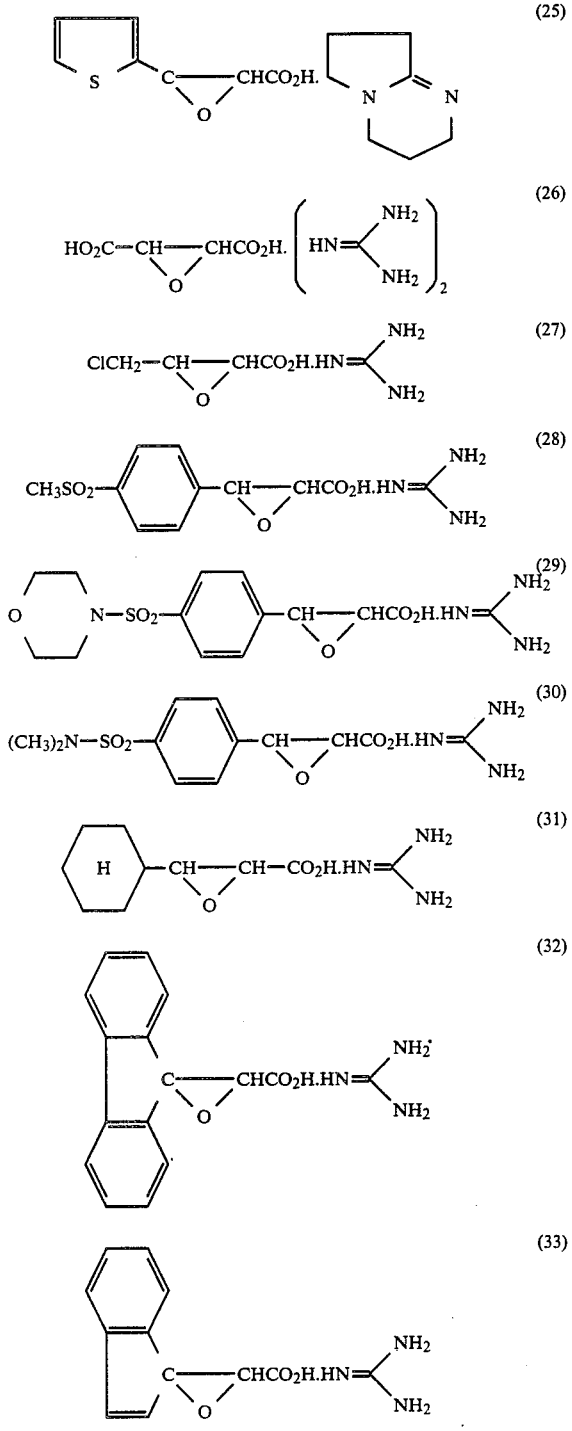

Synthesis of the base precursors of the present invention will be illustrated in detail by presenting some synthesis examples.

SYNTHESIS EXAMPLE SE1

Synthesis of base precursor (12):

To a mixture of 120 g of acetophenone, 123 g of ethyl chloroacetate, and 200 ml of benzene was added 47.2 g of powder sodium amide over a period of 2 hours at 15° C. At the end of a 2-hour stirring at room temperature, the resulting red colored mixture was poured into 700 g of ice water. The organic phase was extracted with benzene, dried, and stripped of the solvent. The residue was fractionally distilled, yielding 130 g of ethyl 3-methyl-3-phenylglycidate having a boiling point of 107°–113° C./3 mmHg.

To a solution of 15.5 g of metallic sodium in 300 ml of ethanol was gradually added 130 g of the ethyl 3-methyl-3-phenylglydidate. The reaction mixture was cooled to 15° C. and gradual addition of 15 ml of water caused exothermic reaction with a sodium salt precipitating out. The reaction mixture was allowed to stand overnight. The crystals were collected by filtration, washed with ethanol, yielding 102 g of sodium 3-methyl-3-phenylglycidate having a melting point of 225°–226° C. (decomposition).

With stirring, 102 g of the sodium 3-methyl-3-phenylglycidate was added to a mixture of 300 g of ice water and 56 ml of concentrated aqueous hydrochloric acid. The precipitating crystals were again collected by filtration, dried, and then dissolved in 250 ml of cold methanol. The solution was neutralized with 80 ml of an aqueous solution containing 43 g of guanidine carbonate. The crystalline deposit was filtered and washed with isopropyl alcohol, yielding 87 g of base precursor (12) having a melting point of 146°–147° C. (decomposition).

SYNTHESIS EXAMPLE SE2

Synthesis of base precursor (8)

Following the procedure of synthesis of ethyl 3-methyl-3-phenylglycidate, ethyl 3-phenylglycidate was prepared according to Darzens' condensation reaction. It had a boiling point of 123°–125° C./18 mmHg.

A mixture of 30 g of the ethyl 3-phenylglycidate, 70 ml of ethanol, 30 ml of water, and 22 g of cyclohexylguanidine was agitated for 3 hours at room temperature and then concentrated by evaporating off some solvent. The crystalline deposit was collected by filtration, yielding 47 g of base precursor (8) having a melting point of 199°–200° C. (decomposition).

SYNTHESIS EXAMPLE SE3

Synthesis of base precursor (15)

A mixture of 151 g of m-nitrobenzaldehyde, 200 g of pyridine, and 120 g of malonic acid was heated for 3 hours with stirring. The mixture was poured into ice water. The resulting crystalline deposit was collected by filtration, washed with water, and dried, yielding 180 g of m-nitrocinnamic acid having a melting point of 156° C.

A mixture of 57.9 g of the m-nitrocinnamic acid, 81 g of sodium hydrogen carbonate, and 3 liters of water was added to a mixture of 102 g of silver nitrate, 96 g of bromine, and 1.5 liters of water. The combined mixture was agitated for one hour at room temperature, rendered acidic again with dilute sulfuric acid, extracted with ether, and dried. The mixture was stripped of the solvent. The residue was recrystallized from carbon tetrachloride/chloroform mixed solvent, yielding 43.2 g of 2-bromo-3-hydroxy-3-(3-nitrophenyl)propanoic acid having a melting point of 124°–125° C.

A mixture of 30.0 g of the 2-bromo-3-hydroxy-3-(3-nitrophenyl)propanoic acid, 30 g of sodium carbonate, and 3 liters of water was heated under reflux, cooled to room temperature, and then made acidic with dilute sulfuric acid. The mixture was extracted with ether, dried, and stripped of the solvent. The residue was recrystallized from benzene, yielding 16.5 g of 3-(3- nitrophenyl)glycidic acid having a melting point of 139°–140° C.

To a mixture of 20.9 g of the 3-(3-nitrophenyl)glycidic acid, 80 ml of ethanol, and 30 ml of water was gradually added 9.0 g of guanidine carbonate. The precipitating crystals were collected by filtration, washed with ethanol, and dried, yielding 23.4 g of base precursor (15) having a melting point of 168°–169° C. (decomposition).

The base precursors of the invention are particularly effective when used together with spectrally sensitized light-sensitive silver halide emulsions. That is, when the precursors are combined with spectrally sensitized light-sensitive silver halide emulsions, image density is increased to a great extent.

The spectral sensitization of silver halide emulsions is achieved with methine dyes and other sensitizing dyes. Examples of the dyes useful for spectral sensitization include cyanine dyes, merocyanine dyes, complex cyanine dyes, complex merocyanine dyes, holopolar cyanine dyes, hemicyanine dyes, styryl dyes, and hemioxonole dyes. Particularly useful dyes are cyanine dyes, merocyanine dyes, and complex merocyanine dyes. For these dyes, any nuclei generally utilized for cyanine dyes can be applied as basic heterocyclic ring nuclei. For example, applicable are pyrroline nuclei, oxazoline nuclei thiazoline nuclei, pyrrole nuclei, oxazole nuclei, thiazole nuclei, selenazole nuclei, imidazole nuclei, tetrazole nuclei, pyridine nuclei, etc.; and nuclei of the foregoing nuclei having cycloaliphatic hydrocarbon rings fused thereto and nuclei of the foregoing nuclei having aromatic hydrocarbon rings fused thereto, such as indolenine nuclei, benzindolenine nuclei, indole nuclei, benzoxazole nuclei, naphthoxazole nuclei, benzothiazole nuclei, naphthothiazole nuclei, benzoselenazole nuclei, benzimidazole nuclei, quinoline nuclei, etc. These nuclei may be substituted on carbon atoms.

For the merocyanine and complex merocyanide dyes, 5- or 6-membered heterocyclic nuclei are applicable as a nucleus having a ketomethylene structure, for example, a pyrazolin-5-one nucleus, thiohydantoin nucleus, 2-thiooxazolidine-2,4-dione nucleus, thiazolidine-2,4-dione nucleus, rhodanine nucleus, thiobarbituric acid nucleus, etc.

These sensitizing dyes may be used alone or in combination. Combinations of sensitizing dyes are often used for supersensitization purposes.

Examples of useful sensitizing dyes are described in, for example, West German Pat. No. 929,080; U.S. Pat. Nos. 2,493,748; 2,503,776; 2,519,001; 2,912,329; 3,656,959; 3,672,897; 3,694,217; 4,025,349; and 4,046,572; U.K. Pat. No. 1,242,588; Japanese Patent Publication Nos. 14,030/69 and 24,844/77.

The amount of the sensitizing dye is from 0.001 g to 20 g, and preferably from 0.01 g to 2 g per 100 g of silver of the silver halide emulsion.

The base precursors of the invention may be used in widely varying amounts. The effective range is 0.001% to 50% by weight, preferably 0.01% to 40% by weight of the total weight of the dry coated layer of a light-sensitive material.

Any unit and layer arrangements may be used with the light-sensitive materials of the present invention. The base precursors may be added to any desired layer in the light-sensitive material, for example, a light-sensitive emulsion layer or a dye-providing-material containing layer when these layers are separately formed, or an intermediate or protective layer, and preferably, the silver halide emulsion layer or a layer adjacent thereto. The base precursors may be used alone or in admixture or two or more.

According to the present invention, silver can be utilized as an image forming substance. Further, various other image forming substances can be employed in various image forming processes.

For instance, couplers may be employed which are capable of forming color images upon reaction with an oxidation product of developing agents which are commonly used in the well-known liquid development. Examples of magenta couplers include 5-pyrazolone couplers, pyrazolobenzimidazole couplers, cyanoacetylcoumarone couplers and open chain acylacetonitrile couplers, etc. Examples of yellow couplers include acylacetamide couplers such as benzoylacetanilides and pivaloylacetanilides, etc. Examples of cyan couplers include naphthol couplers and phenol couplers, etc. It is preferred that these couplers be nondiffusible substances which have a hydrophobic group called a ballast group in the molecule thereof or be polymerized substances. The couplers may be any of the 4-equivalent and 2-equivalent types with respect to silver ion. Further, they may be colored couplers having a color correction effect or couplers which release a development inhibitor as development proceeds (so-called DIR couplers).

Also employable are dyes capable of forming positive color images by a light-sensitive silver dye bleach processes, for example, those described in *Research Disclosure*, No. 14433, pages 30–32 (Apr. 1976), *ibid.*, No. 15227, pages 14–15 (Dec. 1976) and U.S. Pat. No. 4,235,957, etc.; leuco dyes as described, for example, in U.S. Pat. Nos. 3,985,565 and 4,022,617, etc.; and dyes having a nitrogen-containing heterocyclic group introduced as described in *Research Disclosure*, No. 16966, pages 54–58 (May 1978).

In addition, use may be made of dye-providing substances which release a mobile dye by effecting coupling reaction with a reducing agent oxidized by oxidation-reduction reaction with a silver halide or organic silver salt at high temperatures as described in European Pat. Nos. 67,455 and 79,056, West German Pat. No. 3,217,853, etc.; and dye-providing substances which release a mobile dye as the result of oxidation-reduction reaction with a silver halide or organic silver salt at high temperatures as described in European Pat. Nos. 66,282 and 76,492, West German Pat. No. 3,215,485, Japanese Patent Application Nos. 28928/83 and 26008/83, etc.

Preferred dye-providing substances which can be employed in these processes may be represented by the following formula (CI):

$$(\text{Dye-X})_q\text{-Y} \qquad (\text{C I})$$

wherein Dye represents a dye which becomes mobile when it is released from the molecule of the compound represented by formula (C I); X represents a simple bond or a connecting group; Y represents a group which releases Dye in correspondence or countercorrespondence to light-sensitive silver salts having a latent image distributed imagewise, the diffusibility of Dye released being different from that of the compound represented by formula (C I) and q represents an integer of 1 or 2.

The dye represented by Dye is preferably a dye having a hydrophilic group. Examples of the dye which can be used include azo dyes, azomethine dyes, anthraquinone dyes, naphthoquinone dyes, styryl dyes, nitro dyes, quinoline dyes, carbonyl dyes and phthalocyanine dyes, etc. These dyes can also be used in the form having temporarily shortened wavelengths, the color of which is recoverable in the development processing.

More specifically, those dyes described in European Patent Application No. 76,492 may be utilized.

Examples of the connecting group represented by X include —NR— (wherein R represents a hydrogen atom, an alkyl group, or a substituted alkyl group), —SO$_2$—, —CO—, an alkylene group, a substituted alkylene group, a phenylene group, a substituted phenylene group, a naphthylene group, a substituted naphthylene group, —O—, —SO—, or a group derived by combining together two or more of the foregoing groups.

Y in formula (C I) will be described in greater detail.

In one embodiment, Y is selected so that the compound represented by the general formula (C I) is a nondiffusible image-forming compound which is oxidized as a result of development, thereby undergoing self-cleavage and releasing a diffusible dye.

An example of Y which is effective for compounds of this type is an N-substituted sulfamoyl group. For example, a group represented by formula (C II) is illustrated for Y.

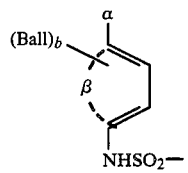

(CII)

wherein

β represents non-metallic atoms necessary for forming a benzene ring, which may optionally be fused with a carbon ring or a hetero ring to form, for example, a naphthalene ring, a quinoline ring, a 5,6,7,8-tetrahydronaphthalene ring, a chroman ring or the like.

α represents a group of —OG$^{11}$ or —NHG$^{12}$ wherein G$^{11}$ represents hydrogen or a group which forms a hydroxy group upon hydrolysis, and G$^{12}$ represents hydrogen, an alkyl group containing 1 to 22 carbon atoms or a hydrolyzable group, Ball represents a ballast group, and b represents an integer of 0, 1 or 2.

Specific examples of Y of this type are described in Japanese Patent Application Kokai Nos. 33826/73 and 50736/78.

Other examples of Y suitable for this type of compound are those represented by the following general formula (C III):

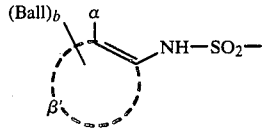

(CIII)

wherein Ball, α, and b are as defined in (C II), β' represents atoms necessary for forming a carbon ring, e.g., a benzene ring which may be fused with another carbon ring or a hetero ring to form a naphthalene ring, quinoline ring, 5,6,7,8-tetrahydronaphthalene ring, chroman ring or the like. Specific examples of Y of this type are described in Japanese Patent Application Kokai Nos. 113624/76, 12642/81, 16130/81, 4043/82 and 650/82, and U.S. Pat. No. 4,053,312.

Further examples of Y suitable for this type of compound are those represented by the following formula (C IV):

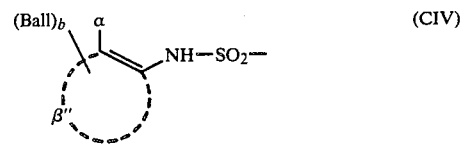

(CIV)

wherein Ball, α, and b are as defined in formula (C II) and β" represents atoms necessary for forming a hetero ring such as a pyrazole ring, a pyridine ring or the like, the hetero ring being optionally bound to a carbon ring or a hetero ring. Specific examples of Y of this type are described in Japanese Patent Application Kokai No. 104343/76.

Still further examples of Y suitable for this type of compound are those represented by the following formula (C V):

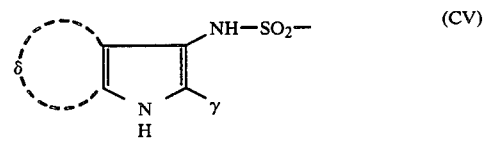

(CV)

wherein γ preferably represent hydrogen, a substituted or unsubstituted alkyl, aryl or heterocyclic group, or —CO—G$^{21}$; where G$^{21}$ represents —OG$^{22}$, —SG$^{22}$ or

(wherein G$^{22}$ represents hydrogen, an alkyl group, a cycloalkyl group or an aryl group, G$^{23}$ is as defined for G$^{22}$, or G$^{23}$ represents an acyl group derived from an aliphatic or aromatic carboxylic or sulfonic acid, and G$^{24}$ represents hydrogen or an unsubstituted or substituted alkyl group); and δ represents a residue necessary for completing a fused benzene ring.

Specific examples of Y of this type are described in Japanese Patent Application Kokai Nos. 104343/76, 46730/78, 130122/79 and 85055/82.

Still further examples of Y suitable for this type of compound are those represented by the formula (C VI):

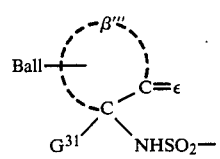

(CVI)

wherein Ball is as defined in formula (C II); ε represents an oxygen atom or =NG$^{32}$ wherein G$^{32}$ represents hydroxy or an optionally substituted amino group, (examples of H$_2$N-G$^{32}$ usable in forming the group =NG$^{32}$ including hydroxylamine, hydrazines, semicarbazides, thiosemicarbazides, etc.); β''' represents a saturated or unsaturated nonaromatic 5-, 6- or 7-membered hydrocarbon ring; and $G^{31}$ represents hydrogen or a halogen atom (e.g., a fluorine atom, a chlorine atom, a bromine atom, etc.).

Specific examples of Y of this type are described in Japanese Patent Application Kokai Nos. 3819/78 and 48534/79.

Other examples of Y of this type of compound are described in Japaense Patent Publication Nos. 32129/73 and 39165/73, Japanese Patent Application Kokai No. 64436/74, U.S. Pat. No. 3,443,934, etc.

Still further examples of Y are those represented by the following formula (C VII):

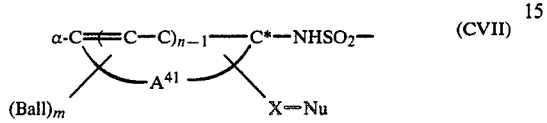

wherein α represents $OR^{41}$ or $NHR^{42}$; $R^{41}$ represents hydrogen or a hydrolyzable component; $R^{42}$ represents hydrogen or an alkyl group containing 1 to 50 carbon atoms; $A^{41}$ represents atoms necessary for forming an aromatic ring; Ball represents an organic immobile group existing on the aromatic ring, with Ball's being the same or different from each other; m represents an integer of 1 or 2; X represents a divalent organic group having 1 to 8 atoms, with the nucleophilic group (Nu) and an electrophilic center (asterisked carbon atom) formed by oxidation forming a 5-to 12-membered ring; Nu represents a nucleophilic group; n represents an integer of 1 or 2; and α may be as defined in formula (C II). Specific examples of Y of this type are described in Japanese Patent Application Kokai No. 20735/82.

Still further examples of the substances represented by formula (C I) are dye-providing, non-diffusible substances which release a diffusible dye in the presence of a base as a result of self cyclization or the like but which, when reacted with an oxidation product of a developing agent, substantially never release the dye.

Examples of Y effective for this type of compound are those which are represented by the formula (C VIII):

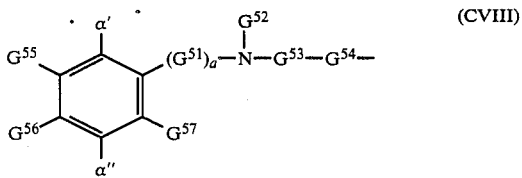

wherein
- α' represents an oxidizable nucleophilic group such as a hydroxy group, a primary or secondary amino group, a hydroxyamino group, and a sulfonamido group, or a precursor thereof;
- α" represents a dialkylamino group or any groups as defined for α';
- $G^{51}$ represents an alkylene group having 1 to 3 carbon atoms;
- a represents 0 or 1;
- $G^{52}$ represents a substituted or unsubstituted alkyl group having 1 to 40 carbon atoms or a substituted or unsubstituted aryl group having 6 to 40 carbon atoms;
- $G^{53}$ represents an electrophilic group such as —CO— or —CS—;
- $G^{54}$ represents an oxygen atom, a sulfur atom, a selenium atom, a nitrogen atom or the like and, when $G^{54}$ represents a nitrogen atom, it may be substituted with hydrogen, a substituted or unsubstituted alkyl group having 1 to 10 carbon atoms or an aromatic residue having 6 to 20 carbon atoms; and
- $G^{55}$, $G^{56}$ and $G^{57}$ each represents hydrogen, a halogen atom, a carbonyl group, a sulfamyl group, a sulfonamido group, an alkyloxy group having 1 to 40 carbon atoms or any groups defined for $G^{52}$, and $G^{55}$ and $G^{56}$, when taken together, may form a 5- to 7-membered ring, and $G^{56}$ may further represent

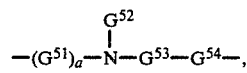

with the proviso that at least one of $G^{52}$, $G^{55}$, $G^{56}$ and $G^{57}$ represents a ballast group. Specific examples of Y of this type are described in Japanese Patent Application Kokai No. 63618/76.

Further examples of Y suitable for this type of compound are those having the following general formulae (C IX) and (C X):

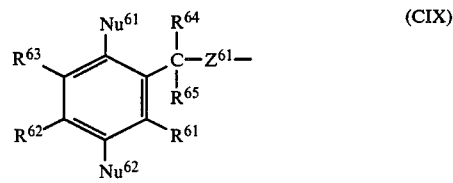

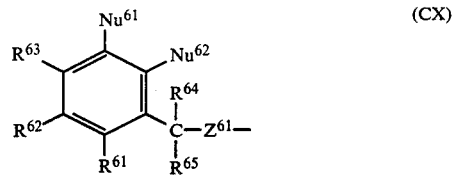

wherein $Nu^{61}$ and $Nu^{62}$ may be the same or different and each represents a nucleophilic group or a precursor thereof; $Z^{61}$ represents a divalent atom group which is electrically negative with respect to the carbon atom substituted by $R^{64}$ and $R^{65}$; $R^{61}$, $R^{62}$ and $R^{63}$ each represents hydrogen, a halogen atom, an alkyl group, an alkoxy group or an acylamino group or, when located at adjacent positions on the ring, $R^{61}$ and $R^{62}$ may form a fused ring together with the rest of the molecule, or $R^{62}$ and $R^{63}$ may form a fused ring together with the rest of the molecule; $R^{64}$ and $R^{65}$ may be the same or different and each represents hydrogen, a hydrocarbon group or a substituted hydrocarbon group; with at least one of the substituents $R^{61}$, $R^{62}$, $R^{63}$, $R^{64}$ and $R^{65}$ having a ballast group, Ball, of a size enough to render the above-described compounds immobile. Specific examples of Y of this type are described in Japanese Patent Application Kokai Nos. 69033/78 and 130927/79.

Further examples of Y suitable for this type of compound are those which are represented by the formula of (CXI):

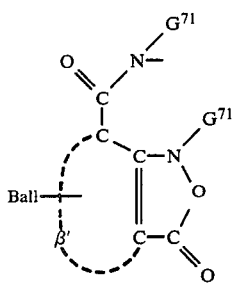

(CXI)

wherein Ball and β' are as defined in formula (C III); and $G^{71}$ represents an alkyl group or a substituted alkyl group. Specific examples of Y of this type are described in Japanese Patent Application Kokai Nos. 111628/74 and 4819/77.

Still another type of compounds having the general formula (C I) include dye-providing, nondiffusible substances which themselves do not release any dye, but release a dye upon reaction with a reducing agent. These compounds may preferably be used in combination with compounds which mediate redox reaction (called electron donors).

Examples of Y effective for this type of compound are those represented by the formula (C XII):

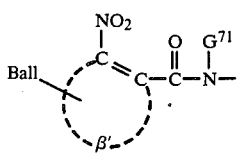

(C XII)

wherein Ball and β' are as defined in the general formula (C III) and $G^{71}$ represents an alkyl group or a substituted alkyl group. Specific examples of Y of this type are described in Japanese Patent Application Kokai Nos. 35533/78 and 110827/78.

Further examples of Y suitable for this type of compound are those having the general formula (C XIII):

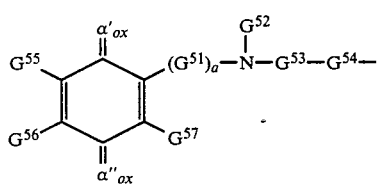

(C XIII)

wherein α'ox and α"ox represent groups capable of giving α' and α" upon reduction, respectively, and α', α", $G^{51}$, $G^{52}$, $G^{53}$, $G^{54}$, $G^{55}$, $G^{56}$, $G^{57}$ and a are as defined in formula (C VIII). Specific examples of Y described above are described in Japanese Patent Application Kokai No. 110827/78, U.S. Pat. Nos. 4,356,249 and 4,358,525.

Further examples of Y suitable for this type of compound are those having the formulae (C XIVA) and (C XIVB):

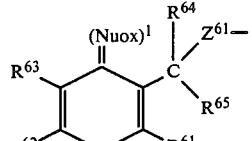

(C XIVA)

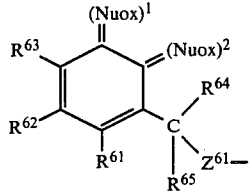

(C XIVB)

wherein $(Nuox)^1$ and $(Nuox)^2$ may be the same or different and each represents an oxidized nucleopholic group, and other notations are the same as defined with respect to formulae (C IX) and (C X). Specific examples of Y of this type are described in Japanese Patent Application Kokai Nos. 130927/79 and 154342/81.

The electron donors which may be used in combination are described in the patents and patent applications which are referred to with respect to formulae (C XII), (C XIII), (C XIVA) and (C XIVB) and incorporated herein by reference.

As still further different type of compound having the general formula (C I), there are illustrated linked donor acceptor (LDA) compounds. These compounds are dye-providing, nondiffusible substances which undergo donor-acceptor reaction in the presence of a base to release a diffusible dye, but upon reaction with an oxidation product of a developing agent, they substantially do not release the dye any more.

Examples of Y effective for this type of compound are those represented by the formula of (C XV):

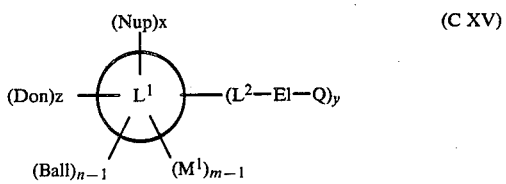

(C XV)

wherein n, x, y, and z each represent 1 or 2, m represents an integer of 1 or more; Don represents a group containing an electron donor or its precursor moiety; $L^1$ represents an organic group linking Nup to —E —Q or Don; Nup represents a precursor of a nucleophilic group; El represents an electrophilic center; Q represents a divalent group; Ball represents a ballast group; $L^2$ represents a linking group; and $M^1$ represents any desired substituent. Specific examples are described in Japanese Patent Application Kokai No. 60289/83.

The ballast group is an organic ballast group which can render the dye-providing substance nondiffusible, and is preferably a group containing a $C_{8-32}$ hydrophobic group. Such organic ballast group is attached to the dye-providing substance directly or through a linking group such as an imino bond, an ether bond, a thioether bond, a carbonamido bond, a sulfonamido bond, a ureido bond, an ester bond, a carbamoyl bond, a sulfamoyl bond, etc., and mixtures thereof.

Two or more types of the dye providing substances may be employed in combination. In such a case two or more types of the dye-providing substances may be used together for purposes of providing the same hue or reproducing black color.

Specific examples of the image forming substances which can be used in the present invention are described in the patents cited hereinbefore. Only some typical, but non-limiting examples are described below because it is difficult and redundant to illustrate all preferred examples. Specific examples of the dye-providing substances having general formula (C I) are set forth below.

CI-1

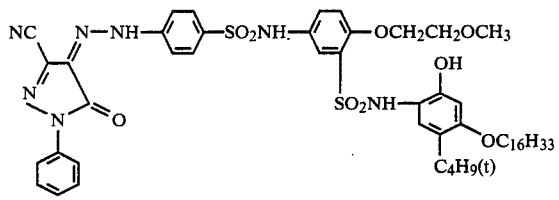

CI-2

CI-3

CI-4

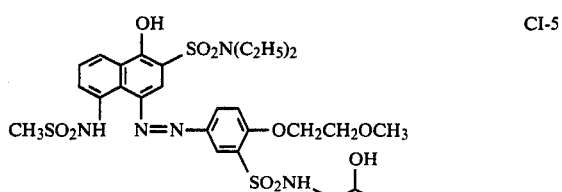

CI-5

CI-6

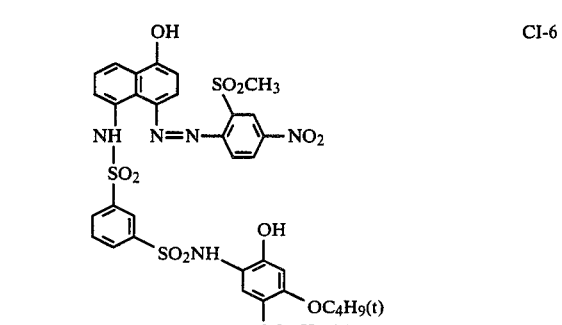

CI-7

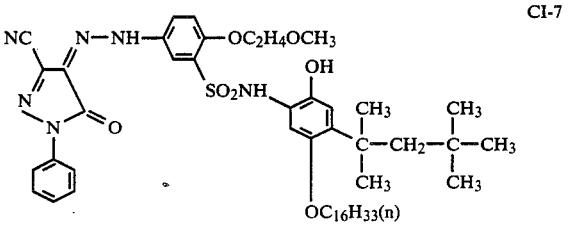

CI-8

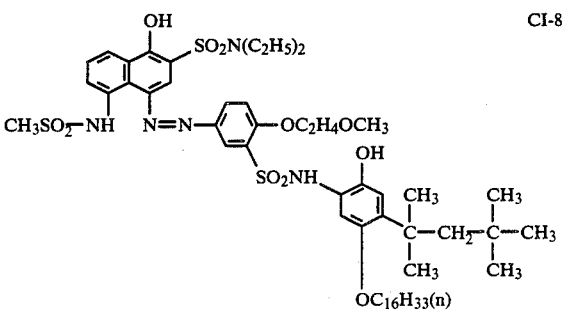

CI-9

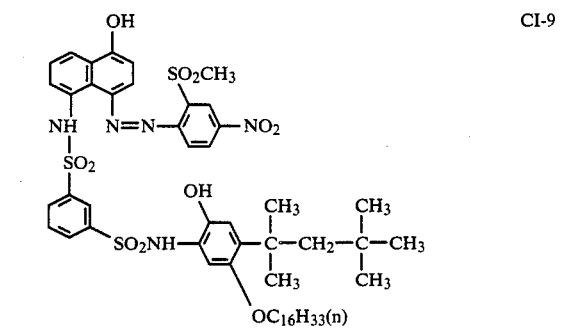

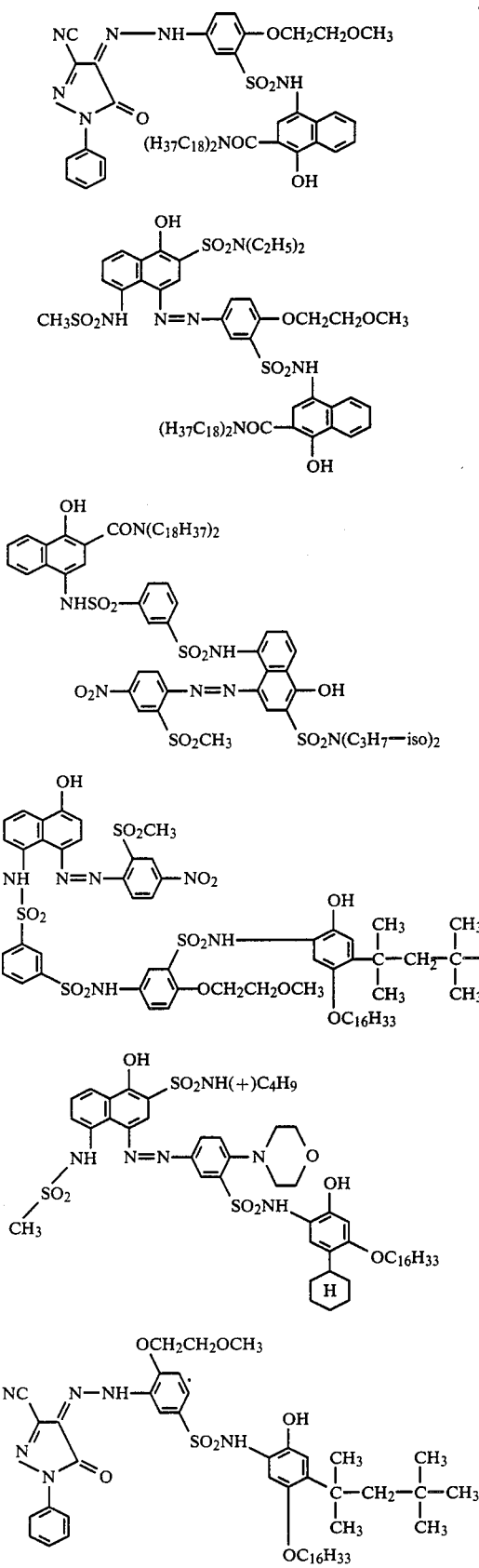

The dye-releasing redox compounds used in the present invention can be introduced into a layer of the light-sensitive material by known methods such as a method as described in U.S. Pat. No. 2,322,027. In this case, an organic solvent having a high boiling point or an organic solvent having a low boiling point as described below can be used. For example, the dye-releasing redox compound is first dissolved in an organic solvent having a high boiling point, for example, a phthalic acid alkyl ester (for example, dibutyl phthalate, dioctyl phthalate, etc.), a phosphoric acid ester (for example, diphenyl phosphate, triphenyl phosphate, tricresyl phosphate, dioctylbutyl phosphate, etc.), a citric acid ester (for example, tributyl acetylcitrate, etc.), a benzoic acid ester (for example, octyl benzoate, etc.), an alkylamide (for example, diethyl laurylamide, etc.), an aliphatic acid ester (for example, dibutoxyethyl succinate, dioctyl azelate, etc.), and a trimesic acid ester (for example, tributyl trimesate, etc.), or an organic solvent having a boiling point of about 30° C. to 160° C., for example, a lower alkyl acetate such as ethyl acetate, butyl acetate, etc., ethyl propionate, sec-butyl alcohol, methyl isobutyl ketone, β-ethoxyethyl acetate, methyl cellosolve acetate, cyclohexanone, etc. Mixtures of the above described high boiling organic solvents and low boiling organic solvents may also be used. The solution of the dye-releasing redox compound may then be dispersed in a hydrophilic colloid.

Further, it is possible to use a method for dispersion in polymers as described in Japanese Patent Publication No. 39853/76 and Japanese Patent Application Kokai No. 59943/76. Moreover, various surface-active agents may be used when the dye-releasing redox compound is dispersed in a hydrophilic colloid. For this purpose, the surface-active agents illustrated in other part of the specification may be used. In the present invention, a reducing agent may be used in the light-sensitive material if necessary. The reducing agents used in the present invention include hydroquinone compounds such as hydroquinone, 2,5-dichlorohydroquinone, 2-chlorohydroquinone, etc.; aminophenol compounds such as 4-aminophenol, N-methylaminophenol, 3-methyl-4-aminophenol, 3,5-dibromo-aminophenol, etc.; catechol compounds such as catechol, 4-cyclohexylcatechol, 3-methoxycatechol, 4-(N-octadecylamino)catechol, etc.; phenylenediamine compounds such as N,N-diethyl-p-phenylenediamine, 3-methyl-N,N-diethyl-p-phenylenediamine, 3-methoxy-N-ethyl-N-ethoxy-p-phenylenediamine, N,N,N',N'-tetramethyl-p-phenylenediamine, etc.

Various combinations of developing agents as described in U.S. Pat. No. 3,039,869 may also be used.

In the present invention, an amount of the reducing agent added is from 0.01 mol to 20 mols per mol of silver and more preferably from 0.1 mol to 10 mols per mol of silver.

The silver halides used in the present invention include silver chloride, silver chlorobromide, silver chloroiodide, silver bromide, silver iodobromide, silver chloroiodobromide and silver iodide, but not limited thereto.

The process for preparing those silver halides is explained with reference to the preparation of silver iodobromide. That is, silver iodobromide is prepared by first adding silver nitrate solution to potassium bromide solution to form silver bromide particles and then adding potassium iodide to the mixture.

Mixtures of two or more silver halides having different particle size and/or halogen composition may be used.

The average particle size of the silver halide used in the present invention is preferably from 0.001 μm to 10 μm and more preferably from 0.001 μm to 5 μm.

The amount of the light-sensitive silver halide coated preferably ranges from 1 mg/m² to 10 g/m² of silver.

The silver halides used in the present invention may be applied with or without chemical sensitization with a chemical sensitizing agent such as compounds of sulfur, selenium or tellurium, etc., or compounds of gold, platinum, palladium, rhodium or iridium, etc., a reducing agent such as tin halide, etc., or a combination thereof. The details thereof are described in T. H. James, *The Theory of the Photographic Process*, the Fourth Edition, Chapter 5, pages 149–169.

In the particularly preferred embodiment of the present invention, an organic silver salt oxidizing agent is used together. The organic silver salt oxidizing agent is a silver salt which forms a silver image by reacting with the above-described image-forming substance or a reducing agent optionally coexisting with the image-forming substance, when it is heated to a temperature of above 80° C. and, preferably, above 100° C. in the presence of exposed silver halide. The co-presence of the organic silver salt oxidizing agent allows the light-sensitive material to provide higher color density.

Examples of such organic silver salt oxidizing agents include those described in U.S. Pat. No. 4,500,626.

A silver salt of an organic compound having a carboxyl group may be used. Typical examples thereof include a silver salt of an aliphatic carboxylic acid and a silver salt of an aromatic carboxylic acid.

In addition, a silver salt of a combound containing a mercapto group or a thione group and a derivative thereof may be used.

Further, a silver salt of a compound containing an imino group may be used. Examples of these compounds include a silver salt of benzotriazole and a derivative thereof as described in Japanese Patent Publication Nos. 30270/69 and 18416/70, for example, a silver salt of benzotriazole, a silver salt of alkyl substituted benzotriazole such as a silver salt of methylbenzotriazole, etc., a silver salt of a halogen substituted benzotriazole such as a silver salt of 5-chlorobenzotriazole, etc., a silver salt of carboimidobenzotriazole such as a silver salt of butylcarboimidobenzotriazole, etc., a silver salt of 1,2,4-triazole or 1-H-tetrazole as described in U.S. Pat. No. 4,220,709, a silver salt of carbazole, a silver salt of saccharin, a silver salt of imidazole and an imidazole derivative, and the like.

Moreover, organic metal salts such as copper stearate and a silver salt as described in *Research Disclosure*, Vol. 170, No. 17029 (June 1978) are included in the organic metal salt oxidizing agents which can be used in the present invention.

Methods of preparing these silver halides and organic silver salt oxidizing agents and blending them are described in *Research Disclosure*, No. 17029, Japanese Patent Application Kokai Nos. 13224/74, 17216/75, 32928/75 and 42529/76, and U.S. Pat. No. 3,700,458.

A total coating amount of the light-sensitive silver halide and the organic silver salt oxidizing agent employed in the present invention preferably ranges from 50 mg/m² to 10 g/m² of silver.

In the practice of the present invention, the binders may be employed alone or in combinations thereof. A hydrophilic binder may be used as the binder according to the present invention. The typical hydrophilic binder is a transparent or translucent hydrophilic colloid, examples of which include natural substances, for example, proteins such as gelatin, a gelatin derivative, a cellulose derivative, etc., a polysaccharide such as starch, gum arabic, etc., and a synthetic polymer, for example, a water-soluble polyvinyl compound such as polyvinyl alcohol, polyvinyl pyrrolidone, acrylamide polymer, etc. Another example of the synthetic polymer compound is a dispersed vinyl compound in a latex form which is used for the purpose of increasing dimensional stability of a photographic material.

Further, in the present invention, it is possible to use a compound which activates development simultaneously with stabilizing the image. Particularly, it is preferred to use isothiuroniums including 2-hydroxyethylisothiuronium trichloroacetate as described in U.S. Pat. No. 3,301,678, bisisothiuroniums including 1,8-(3,6-dioxaoctane)bis(isothiuronium trifluoroacetate) etc., as described in U.S. Pat. No. 3,669,670, thiol compounds as described in German Patent Application (OLS) No. 2,162,714, thiazolium compounds such as 2-amino-2-thiazolium trichloroacetate, 2-amino-5-bromoethyl-2-thiazolium trichloroacetate, etc., as described in U.S. Pat. No. 4,012,260, compounds having α-sulfonylacetate as an acid part such as bis(2-amino-2-thiazolium)-methylenebis(sulfonylacetate), 2-amino-2-thiazolium phenylsulfonylacetate, etc., as described in U.S. Pat. No. 4,060,420, and compounds having 2-carboxycarboxamide as an acid part as described in U.S. Pat. No. 4,088,496.

The photosensitive materials of the present invention may contain a toning agent if desired. Effective toning agents are 1,2,4-triazoles, 1H-tetrazoles, thiouracils, 1,3,4-thiadiazoles, and similar compounds. Examples of preferred toning agents include 5-amino-1,3,4-thiadiazole-2-thiol, 3-mercapto-1,2,4-triazole, bis(dimethylcarbamyl)disulfide, 6-methylthiouracil, 1-phenyl-2-tetrazoline-5-thione, and the like. Particularly effective toning agents are compounds which can impart a black color tone to images.

The content of such a toning agent as described above generally ranges from about 0.001 to 0.1 mol per mol of silver in the photosensitive material although the exact content depends upon the type of a heat developable photosensitive material used, processing conditions, desired images and various other factors.

The above-described bases or base precursors may be used not only for the acceleration of dye release but also for other purposes such as pH control.

The above-described various ingredients to constitute a heat developable photosensitive material may be arranged in arbitrary positions, if desired. For instance, one or more of the ingredients may be incorporated in one or more of the constituent layers of a photosensitive material, if desired. In some cases, it is desired that particular proportions of reducing agent, image stabilizing agent and/or other additives be distributed in a protective layer. Such distribution of additives can reduce migration of additives among constituent layers of a heat developable photosensitive material and is thus of advantage in some cases.

The heat developable photosensitive materials of the present invention are effective in forming both negative and positive images. The negative or positive image can be formed depending mainly on the type of the light-sensitive silver halide. For instance, in order to produce direct positive images, internal image type silver halide emulsions described in U.S. Pat. Nos. 2,592,250, 3,206,313, 3,367,778 and 3,447,927, or mixtures of surface image type silver halide emulsions with internal image type silver halide emulsions as described in U.S. Pat. No. 2,996,382 may be used.

Various means of exposure may be used in the present invention. Latent images are obtained by imagewise exposure by radiant rays including visible rays. Generally, light sources used for conventional color prints may be used, examples of which include tungsten lamps, mercury lamps, halogen lamps such as iodine lamps, xenon lamps, laser light sources, CRT light sources, fluorescent tubes and light-emitting diodes, etc.

In the present invention, after the heat-developable color photographic material is exposed to light, the resulting latent image can be developed by heating the material to a suitable elevated temperature. A higher or lower temperature can be utilized to prolong or shorten the heating time insofar as it is within the above-described temperature range.

Any desired heating means may be used, for example, a simple heat plate, iron, heat roller, heat generator utilizing carbon or titanium white, and the like.

The support and the optional dye-fixing material used in the light-sensitive material according to the present invention must withstand the processing temperature. As an ordinary support, not only glass, paper, metal and analogues, but also an acetyl cellulose film, a cellulose ester film, a polyvinyl acetal film, a polystyrene film, a polycarbonate film, a polyethylene terephthalate film, and a film related thereto or a plastic material may be used. Further, a paper support laminated with a polymer such as polyethylene, etc. may be used. Those polyesters described in U.S. Pat. Nos. 3,634,089 and 3,725,070 are preferably used.

In the photographic light-sensitive material and the dye-fixing material of the present invention, the photographic emulsion layer and other binder layers may contain inorganic or organic hardeners. It is possible to use chromium salts such as chromium alum, chromium acetate, etc.; aldehydes such as formaldehyde, glyoxal, glutaraldehyde, etc.; N-methylol compounds such as dimethylolurea, methylol dimethylhydantoin, etc.; dioxane derivatives such as 2,3-dihydroxydioxane, etc.; active vinyl compounds such as 1,3,5-triacryloyl-hexahydro-s-triazine, 1,3-vinylsulfonyl-2-propanol, etc.; active halogen compounds such as 2,4-dichloro-6-hydroxy-s-triazine, etc.; mucohalogenic acids such as mucochloric acid, mucophenoxychloric acid, etc. or the like alone or in combinations of two or more.

The transfer of dyes from the light-sensitive layer to the dye-fixing layer can be carried out using a dye transfer assistant.

The dye transfer assistants suitably used in supplying them from outside the system include water and an aqueous solution containing sodium hydroxide, potassium hydroxide or an inorganic alkali metal salt. Further, a low boiling solvent such as methanol, N,N-dimethylformamide, acetone, diisobutyl ketone, etc., and a mixture of such a low boiling solvent with water or alkaline aqueous solution can be used. The dye transfer assistant may be used by wetting the image receiving layer with the transfer assistant.

When the dye transfer assistant has been incorporated into the light-sensitive material or the dye-fixing material, the transfer assistant need not be supplied from the outside. The above-described dye transfer assistant may be incorporated into the material in the form of water of crystallization or microcapsules or as a precursor which releases a solvent at a high temperature.

More preferably, a hydrophilic thermal solvent which is solid at an ambient temperature and melts at a high temperature may be incorporated into the light-sensitive material or the dye-fixing material. The hydrophilic thermal solvent may be incorporated in the light-sensitive material and/or the dye fixing material. Although the solvent can be incorporated into any of the emulsion layer, the intermediate layer, the protective layer and the dye fixing layer, it is preferred to incorporate it into the dye fixing layer and/or layers adjacent thereto.

Examples of the hydrophilic thermal solvents include ureas, pyridines, amides, sulfonamides, imides, alcohols, oximes and other heterocyclic compounds.

Other compounds which can be used in the photosensitive material of the present invention, for example, sulfamide derivatives, cationic compounds containing a pyridinium group, surface active agents having polyethylene oxide chains, sensitizing dyes, antihalation and antiirradiation dyes, hardeners, mordants and so on, are those described in U.S. Pat. Nos. 4,500,626, 4,478,927, 4,463,079, and 4,503,137 and Japanese Patent Application No. 28928/83 (corresponding to U.S. patent application Ser. No. 582,655 filed on Feb. 23, 1984). Exposure and other techniques disclosed in the above-described patents may also be employed in the present invention.

The light-sensitive materials of the present invention may further contain other additives which are generally employed in such materials, for example, sulfamide derivaties, cationic compounds having pyridinium radical or the like, surfactants having a polyethylene oxide chain, halation- and irradiation-inhibiting dyes, hardening agents, and mordants as disclosed in European Patent Application (published) Nos. 76,492 and 66,282; West German Pat. No. 3,315,485; and Japanese Patent Application Nos. 28,928/'83 and 26,008/'83. Any desired methods for exposure, development and post-treatments may be applied to the heat developable light-sensitive materials of the present invention as disclosed in the patent specifications previously incorporated herein by reference.

The heat developable light-sensitive materials containing a base precursor in the form of a compound having formula [I] as defined above according to the present invention can produce images having a high density within a short time. Another benefit is improved shelf stability in that they experience little change in photographic characteristics during aging.

EXAMPLES

In order that those skilled in the art may better understand how the present invention may be practiced, the following examples are given by way of illustration and not by way of limitation.

EXAMPLE 1

Preparation of Silver Iodobromide Emulsion

Gelatin (40 g) and KBr (26 g) were dissolved in water (3,000 ml). The solution was agitated at 50° C. A solution of silver nitrate (34 g) in water (200 ml) and a 200 ml portion of a solution of dye I (0.02 g) shown hereinafter in methanol (300 ml) were added to the KBr solution over a period of 10 minutes. To this solution, a solution of KI (3.3 g) in water (100 ml) was added over a period of 2 minutes. The thus prepared silver idobromide emulsion was adjusted to such pH that an excess salt precipitated out of the emulsion, and the excess salt filtered off. The emulsion was then adjusted to pH 6.0 to obtain a silver iodrobomide emulsion (yield: 400 g).

Dye I

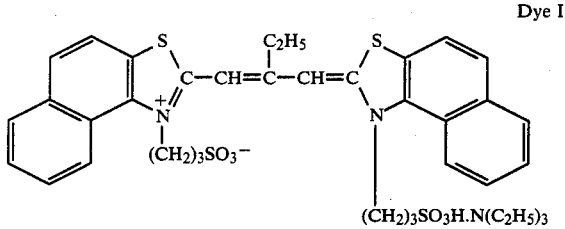

Preparation of Coupler Dispersion in Gelatin

Five grams of 2-dodecylacarbamoyl-1-naphthol, dye providing material (17) was dissolved together with 0.5 g of succinic acid-2-ethylhexyl ester sodium sulfonate surfactant and 2.5 g of tricresyl phosphate (TCP) solvent were dissolved in 30 ml of ethyl acetate. The solution was mixed with 100 g of a 10 wt % gelatin solution by agitation. The mixture was dispersed using a homogenizer for 10 minutes at 10,000 rpm.

A coating liquid having the composition indicated below was applied to a polyethylene terephthalate base film to a wet thickness of 60 μm and then dried to form a light-sensitive material.

| | | |
|---|---|---|
| (a) | Silver iodobromide emulsion | 10 g |
| (b) | Coupler dispersion in gelatin | 3.5 g |
| (c) | Base precursor (7) of the invention | 0.19 g |
| (d) | Gelatin (10 wt %) aqueous solution | 5 g |
| (e) | Solution of 0.2 g of 2,6-dichloro-p-aminophenol in 17 ml of water | |

The light-sensitive material thus prepared was imagewise exposed under a tungsten lamp of 2,000 lux for 5 seconds. Then, the exposed material was uniformly heated on a heat block at 150° C. for 20 seconds to produce a negative cyan dye image. The image density was measured with a Macbeth transmission densitometer (Model TD-504): Dmax 2.19 and Dmin 0.18.

The above result indicates that the base precursor according to the present invention provides a high density.

The same light-sensitive material was aged at 60° C. for 2 days before it was processed by the same procedure as above. The image density was measured to be Dmax 2.20 and Dmin 0.28, indicating excellent aging stability.

EXAMPLE 2

This example used a silver iodobromide emulsion of the same type as used in Example 1 and a dispersion of dye releasing material prepared as follows.

Preparation of Dispersion of Dye Releasing Material

Five grams of a dye releasing material CI-2 was dissolved together with 0.5 g of succinic acid-2-ethylhexyl ester sodium sulfonate surfactant and 5 g of tricresyl phosphate (TCP) solvent in 30 ml of ethyl acetate by heating at about 60° C. The solution was mixed with 100 g of a 10 wt % gelatin solution by agitation, and the mixture was dispersed using a homogenizer for 10 minutes at 10,000 rpm.

A light-sensitive coating composition was prepared from the following formulation.

| | | |
|---|---|---|
| (a) | Light-sensitive silver iodobromide emulsion (as prepared in Example 1) | 25 g |
| (b) | Dispersion of dye releasing material CI-2 | 33 g |
| (c) | Aqueous solution of 5 wt % compound having the formula: $C_9H_{19}-\phi-O(CH_2CH_2O)_{10}H$ | 10 ml |
| (d) | Aqueous solution of 10 wt % compound having the formula: $H_2NSO_2N(CH_3)_2$ | 4 ml |
| (e) | Base precursor (7) of the invention | 1.79 g |
| (f) | Water | 20 ml |

Components (a) to (f) were combined and dissolved by heating. The solution was applied onto a polyethylene terephthalate film base to a wet thickness of 30 μm and then dried to form a light-sensitive material. This material was imagewise exposed under a tungsten lamp of 2,000 lux for 10 seconds and uniformly heated on a heat block at 150° C. for 20 seconds to provide sample A.

Sample B was prepared by the same procedure as above except that 1.8 g of guanidine trichloroacetic acid was used as component (e) in place of base precursor (7) of this invention in Sample A, Sample C prepared using 2.1 g of guanidine phenylsulfonylacetate instead and Sample D prepared using 2.2 g of guanidine 3-sulfamoylphenylsulfonylacetate instead. These samples were processed in the same manner as above.

Preparation of Image-receiving Material

Ten grams of methyl acrylate-co-N,N,N-trimethyl-N-vinylbenzylammonium chloride copolymer (molar ratio of methyl acrylate to vinylbenzyl ammonium chloride 1:1) was dissolved in 200 ml of water, and the solution was homogeneously mixed with 100 g of 10 wt % lime-treated gelatin. The resulting mixture was uniformly spread onto a paper substrate laminated with polyethylene having TiO₂ dispersed, thereby forming an image-receiving layer having a uniform wet thickness of 90 μm. The layer was dried to provide an image-receiving material.

The image-receiving material was dipped in water and recovered therefrom. Each of Samples A, B, C and D of the light-sensitive materials was heated and superimposed on a piece of the image-receiving material in such a manner that the light-sensitive layer was in contact with the image-receiving layer.

After heating on a heat block at 80° C. for 6 seconds, the image-receiving materials were peeled from the light-sensitive materials to find that negative magenta color images were formed on the image-receiving materials. The negative images were measured for maximum and minimum densities with a Macbeth (RD-519) reflection densitometer.

Samples A, B, C and D were aged at 60° C. for 2 days before they were processed by the same procedure as above. The resultant negative images were measured for maximum density (D'max) and minimum density (D'min).

The results are shown in Table 1.

TABLE 1

| Sample No. | Dmax | Dmin | D'max | D'min |
|---|---|---|---|---|
| A (Invention) | 2.15 | 0.16 | 2.16 | 0.35 |
| B (Comparison) | 2.14 | 0.58 | overall fogging | |
| C (Comparison) | 1.28 | 0.16 | 1.33 | 0.20 |
| D (Comparison) | 1.45 | 0.15 | 1.49 | 0.27 |

The data in Table 1 shows that the base precursor according to the present invention gives high maximum and low minimum densities and has excellent aging stability.

EXAMPLE 3

The procedure of Example 2 was repeated except that the base precursors shown in Table 2 were used. The results are also shown in the same table.

TABLE 2

| Sample No. | Base Precursor, Amount | Dmax | Dmin | D'max | D'min |
|---|---|---|---|---|---|
| E | Compound (18) 2.19 g | 2.16 | 0.18 | 2.18 | 0.26 |
| F | Compound (24) 1.83 g | 2.05 | 0.13 | 2.13 | 0.25 |
| G | Compound (29) 2.98 g | 2.01 | 0.16 | 2.14 | 0.35 |

The data in Table 2 shows that base precursors according to the present invention give high maximum and low minimum densities and has excellent aging stability.

EXAMPLE 4

This example used an organic silver salt oxidizing agent.

Preparation of Silver Benzotriazole Emulsion

Gelatin (28 g) and benzotriazole (13.2 g) were dissolved in water (3,000 ml). The resulting solution was agitated at 40° C. A solution of silver nitrate (17 g) in water (100 ml) was added to the solution over a period of 2 minutes.

The resulting benzotriazole silver emulsion was adjusted to such pH that an excess salt precipitated, and the excess salt was filtered off. The emulsion was then adjusted to pH 6.0, obtaining a silver benzotriazole emulsion in a yield of 400 g.

Using the silver benzotriazole emulsion, a light-sensitive coating composition was prepared from the following formulation.

| | | |
|---|---|---|
| (a) | Silver iodobromide emulsion (as prepared in Example 1) | 20 g |
| (b) | Silver benzotriazole emulsion | 10 g |
| (c) | Dispersion of dye releasing material (as prepared in Example 2) | 33 g |
| (d) | Aqueous solution of 5 wt % compound having the formula: $C_9H_{19}\text{—}\langle\bigcirc\rangle\text{—}O\text{-}(CH_2CH_2O)_{10}\text{-}H$ | 10 ml |
| (e) | Aqueous solution of 10 wt % compound having the formula: $H_2NSO_2N(CH_3)_2$ | 4 ml |
| (f) | Base precursor (7) of the invention | 1.79 g |
| (g) | Gelatin dispersion of the acid precursor shown below | 8 ml |
| (h) | Water | 12 ml |

The gelatin dispersion of the acid precursor as component (g) was prepared as follows.

To 100 g of 1% aqueous solution of gelatin was added 10 g of the compound shown below. The mixture was pulverized for 10 minutes in a mill filled with 100 g of glass beads having a mean particle size of about 0.6 mm. By separating the glass beads by filtration, a gelatin dispersion of the acid precursor was obtained

[Chemical structure: naphthalene with CH=N—O—C(=O)—phenyl and OCH₂—phenyl substituents]

Components (a) to (g) were combined. Using the mixture, Samples A', B', and C' were prepared by following the same procedure as in Example 2. The samples were also processed as in Example 2. The results are shown below.

| | Sample | Dmax | Dmin |
|---|---|---|---|
| (A') | Containing base precursor (7) (Invention) | 2.08 | 0.14 |
| (B') | Containing guanidine trichloroacetic acid (Comparison) | 2.33 | 0.61 |
| (C') | Containing guanidine phenylsulfonylacetate (Comparison) | 1.47 | 0.19 |

This data reveals that the sample containing the base precursor of the present invention gives high maximum density and low minimum density.

Further, Samples A', B', and C' were aged for 2 days at 60° C. before they were processed in the same manner as above. It was found that the minimum density and the maximum density were 0.14 and 2.08, respectively, for sample A' and 0.20 and 1.52, respectively, for Sample C', while Sample B' fogged overall. As seen from the date the sample of this invention show good aging stability.

EXAMPLE 5

Preparation of Silver Benzotriazole Emulsion Containing Light-sensitive Silver Bromide Benzotriazole (6.5 g) and gelatin (10 g) were dissolved in water (1,000 ml). The resulting solution was agitated at 50° C. A solution of silver nitrate (8.5 g) in water (100 ml) was added to the solution over a period of 2 minutes.

Then, a solution of potassium bromide (1.2 g) in water (50 ml) was added to the combined solution over a period of 2 minutes. The thus prepared emulsion was adjusted to such pH that an excess salt precipitated out of the emulsion, and the excess salt was filtered off. The emulsion was adjusted to pH 6.0, obtaining a silver benzotriazole emulsion in a yield of 200 g.

Preparation of Gelatin Dispersion of Dye Releasing Material

Ten grams of dye releasing material CI-16 having the following formula:

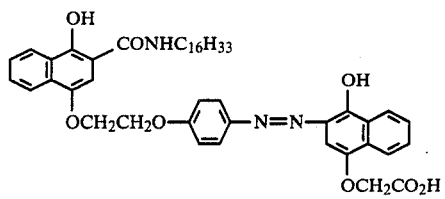

CI-16 was dissolved together with 0.5 g of succinic acid-2-ethylhexyl ester sodium sulfonate and 4 g of tricresyl phosphate (TCP) in 20 ml of cyclohexanone by heating at about 60° C., obtaining a homogeneous solution. The solution was mixed with 100 g of a 10 wt % solution of lime-treated gelatin by agitation, and the mixture was dispered with a homogenizer for 10 minutes at 10,000 rpm.

A coating composition for light-sensitive material was prepared from the following formulation.

| | | |
|---|---|---|
| (a) | Silver benzotriazole emulsion containing light-sensitive silver bromide | 10 g |
| (b) | Dispersion of dye releasing material | 3.5 g |
| (c) | Base precursor (7) of the invention | 0.19 g |
| (d) | Gelatin (10 wt % aqueous solution) | 5 g |
| (e) | Solution of 200 ml of 2,6-dichloro-4-amino-phenol in 4 ml of methanol | |

Components (a) to (e) were mixed and dissolved by heating. The solution was applied onto a polyethylene terephthalate film of 180 μm thick to form a light-sensitive layer having a wet thickness of 30 μm. The web was dried and imagewise exposed under a tungsten lamp of 2000 lux for 10 seconds and then uniformly heated on a heat block at 150° C. for 20 seconds.

The heated sample of light-sensitive material was superimposed on an image-receiving material as prepared in Example 2 and subsequently processed as in Example 2, producing a negative magenta color image on the image-receiving material. Measurement with a Macbeth (RD-519) reflection densitometer showed that the negative image had Dmax 2.17 and Dmin 0.15.

The compound of the present invention was found to exhibit excellent effects.

EXAMPLE 6

Preparation of Gelatin Dispersion of Dye Releasing Material CI-17

Five grams of dye releasing material CI-17 having the structural formula:

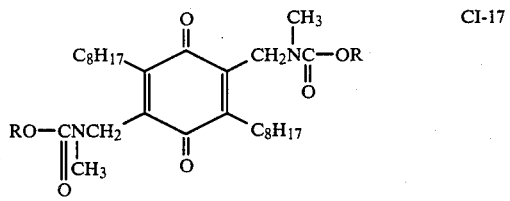

CI-17 where R is

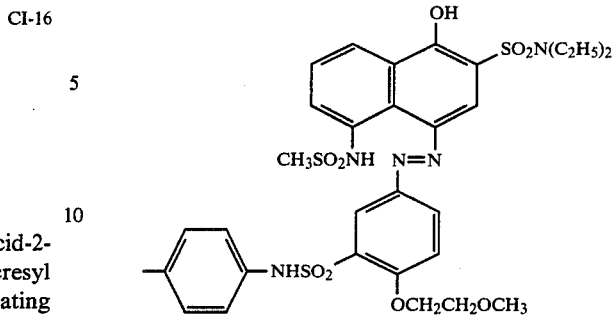

and four grams of an electron donor having the structural formula:

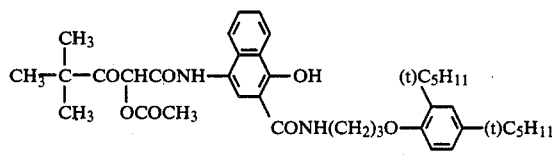

were dissolved together with 0.5 g of succinic acid-2-ethylhexyl ester sodium sulfonate surfactant and 10 g of tricresyl phosphate (TCP) solvent in 20 ml of cyclohexanone by heating at about 60° C. The solution was mixed with 100 g of 10 wt % gelatin solution by agitation, and the mixture was dispersed with a homogenizer for 10 minutes at 10,000 rpm.

A coating composition for light-sensitive material was prepared from the following formulation.

| | | |
|---|---|---|
| (a) | Silver benzotriazole emulsion containing light-sensitive silver bromide (as prepared in Example 5) | 10 g |
| (b) | Dispersion of dye releasing material (prepared in this Example) | 3.5 g |
| (c) | Base precursor (7) of the invention | 0.19 g |
| (d) | Aqueous solution of 5 wt % compound having the formula: $C_9H_{19}\text{-}\phi\text{-}O(CH_2CH_2O)_8H$ | 1.5 ml |
| (e) | Water | 4 ml |

Components (a) to (e) were mixed and dissolved by heating. The resulting solution was applied to a polyethylene terephthalate film to form a light-sensitive layer having a wet thickness of 30 μm. The web was dried and imagewise exposed under a tungsten lamp of 2000 lux for 10 seconds and then uniformly heated on a heat block at 140° C. for 40 seconds.

The heated sample of light-sensitive material was superimposed on an image-receiving material as prepared in Example 2 and previously impregnated with water, and subsequently processed as in Exmaple 2, producing a positive magenta color image on the image-receiving material. Measurement with a Macbeth (RD-519) reflection densitometer using green light showed that the image had Dmax 2.14 and Dmin 0.12.

The base precursor of the present invention was found to exhibit excellent effects.

While the invention has been described with reference to specific embodiments thereof, it will be apparent to one skilled in the art that various changes and modifications can be made therein without departing from the spirit and scope of the invention.

What is claimed is:

1. A heat developable light-sensitive material comprising a support and a heat developable light-sensitive layer containing a silver halide formed thereon wherein said light-sensitive material contains as a base precursor at least one compound selected from the group consisting of compounds having the formula [I]:

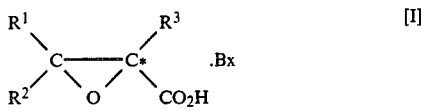

wherein
- $R^1$ and $R^2$ individually represent a hydrogen atom, a substituted or unsubstituted alkyl group, a substituted or unsubstituted cycloalkyl group, a substituted or unsubstituted alkenyl group, a substituted or unsubstituted alkynyl group, a substituted or unsubstituted aryl group, a substituted or unsubstituted aralkyl group, a substituted or unsubstituted heterocyclic group, or —$CO_2M$ wherein M represents a hydrogen atom, an alkali metal or H.Bx, and $R^1$ and $R^2$ can be joined together to form a ring;
- $R^3$ represents a hydrogen atom, a substituted or unsubstituted alkyl group, a substituted or unsubstituted cycloalkyl group, a substituted or unsubstituted alkenyl group, a substituted or unsubstituted alkynyl group, a substituted or unsubstituted aralkyl group, a substituted or unsubstituted aryl group, or a substituted or unsubstituted heterocyclic group;
- B represents a monoacidic organic base or diacidic organic base;
- x is equal to 1 when B represents a monoacidic base and equal to ½ when B represents a diacidic base; and
- C* represents an asymmetric carbon atom to which $R^3$ and $CO_2H$ may be attached in either of the possible configurations.

2. A heat developable light-sensitive material as set forth in claim 1 wherein B is an organic acid base having a pKa of at least 9 and containing not more than 10 carbon atoms.

3. A heat developable light-sensitive material as set forth in claim 2 wherein B has a boiling point of at least 100° C.

4. A heat developable light-sensitive material as set forth in claim 3 wherein B is a monoacidic or diacidic, nitrogen containing, sulfur-free base.

5. A heat developable light-sensitive material as set forth in claim 2 wherein B represents an organic base selected from the group consisting of an aromatic or aliphatic amine, an aromatic or aliphatic diamine, a piperidine, a piperadine, a guanidine, a cyclic guanidine, an amidine, a cyclic amidine, and a tetraalkylammonium hydroxide.

6. A heat developable light-sensitive material as set forth in claim 1 wherein one of $R^1$ and $R^2$ is a substituted or unsubstituted alkyl, aryl or heterocyclic group, and the other is a hydrogen atom or a substituted or unsubstituted alkyl or aryl group.

7. A heat developable light-sensitive material as set forth in claim 1 wherein the substituent on said substituted groups represented by $R^1$ and $R^2$ is selected from the group consisting of an alkoxy or aryloxy group, an alkyl- or arylsulfonyl group, a sulfamoyl group, an N-alkyl- or N-arylsulfamoyl group, a carbamoyl group, an N-alkyl- or N-arylcarbamoyl group, an alkyl- or aryl-sulfonamido group, an alkyl- or arylacyl amido group, a halogen atom, a nitro group, and a cyano group.

8. A heat developable light-sensitive material as set forth in claim 1 wherein said base precursor is incorporated in an amount of from 0.001 to 50% by weight based on the total weight of the dry coated layer of the light-sensitive material.

9. A heat developable light-sensitive material as set forth in claim 1 wherein said heat developable light-sensitive layer is comprised of a silver halide emulsion layer.

10. A heat developable light-sensitive material as set forth in claim 9 wherein said silver halide emulsion contains a sensitizing dye.

11. A heat developable light-sensitive material as set forth in claim 10 wherein the amount of the sensitizing dye is from 0.001 to 20 g per 100 g of silver of the silver halide emulsion.

12. A heat developable light-sensitive material as set forth in claim 9 wherein said base precursor is incorporated in the silver halide emulsion layer or a layer adjacent thereto.

13. A heat developable light-sensitive material as set forth in claim 9 wherein the light-sensitive material further comprises an image fixing layer provided on a support other than that for the light-sensitive layer, and said base precursor is incorporated in the image fixing layer.

14. A method for producing an image, which comprises heat developing a heat developable light-sensitive material comprising a support and a heat developable light-sensitive layer containing a silver halide formed thereon, said light-sensitive material contains as a base precursor at least one compound selected from the group consisting of compounds represented by formula [I]:

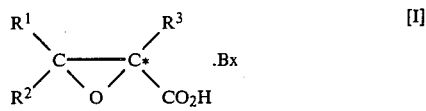

wherein
- $R^1$ and $R^2$ individually represent a hydrogen atom, a substituted or unsubstituted alkyl group, a substituted or unsubstituted cycloalkyl group, a substituted or unsubstituted alkenyl group, a substituted or unsubstituted alkynyl group, a substituted or unsubstituted aryl group, a substituted or unsubstituted aralkyl group, a substituted or unsubstituted heterocyclic group, or —$CO_2M$ wherein M represents a hydrogen atom, an alkali metal or H.Bx, and $R^1$ and $R^2$ can be joined together to form a ring;
- $R^3$ represents a hydrogen atom, a substituted or unsubstituted alkyl group, a substituted or unsubstituted cycloalkyl group, a substituted or unsubstituted alkenyl group, a substituted or unsubstituted alkynyl group, a substituted or unsubstituted aralkyl group, a substituted or unsubstituted aryl group, or a substituted or unsubstituted heterocyclic group;
- B represents a monoacidic organic base or diacidic organic base;
- x is equal to 1 when B represents a monoacidic base and equal to ½ when B represents a diacidic base; and
- C* represents an asymmetric carbon atom to which $R^3$ and $CO_2H$ may be attached in either of the possible configurations.

* * * * *